US00PP22402P3

(12) United States Plant Patent
Skotak

(10) Patent No.: US PP22,402 P3
(45) Date of Patent: Dec. 27, 2011

(54) ***ANANAS* PLANT NAMED 'DURANAS'**

(50) Latin Name: *Ananas comosus*
Varietal Denomination: Duranas

(76) Inventor: Chester Skotak, Alajuela (CR)

( * ) Notice: Subject to any disclaimer, the term of this patent is extended or adjusted under 35 U.S.C. 154(b) by 0 days.

(21) Appl. No.: 12/592,560

(22) Filed: Nov. 27, 2009

(65) Prior Publication Data

US 2011/0131691 P1 Jun. 2, 2011

(51) Int. Cl.
*A01H 5/00* (2006.01)

(52) U.S. Cl. ..... Plt./156
(58) Field of Classification Search ..... Plt./156
See application file for complete search history.

(56) References Cited

OTHER PUBLICATIONS

Plants Profile Ananas comosus, 2010, retrieved on Dec. 2, 2010. Retrieved from the Internet at <http://plants.usda.gov/java/profile?symbol=ANCO30> 3 pp.*

* cited by examiner

*Primary Examiner* — June Hwu

(57) ABSTRACT

A new and distinct *Ananas comosus* cultivar named 'Duranas' is disclosed, characterized by a compact, bushy plant shape, small fruit and suitability as an indoor pot plant.

1 Drawing Sheet

Figure 1:
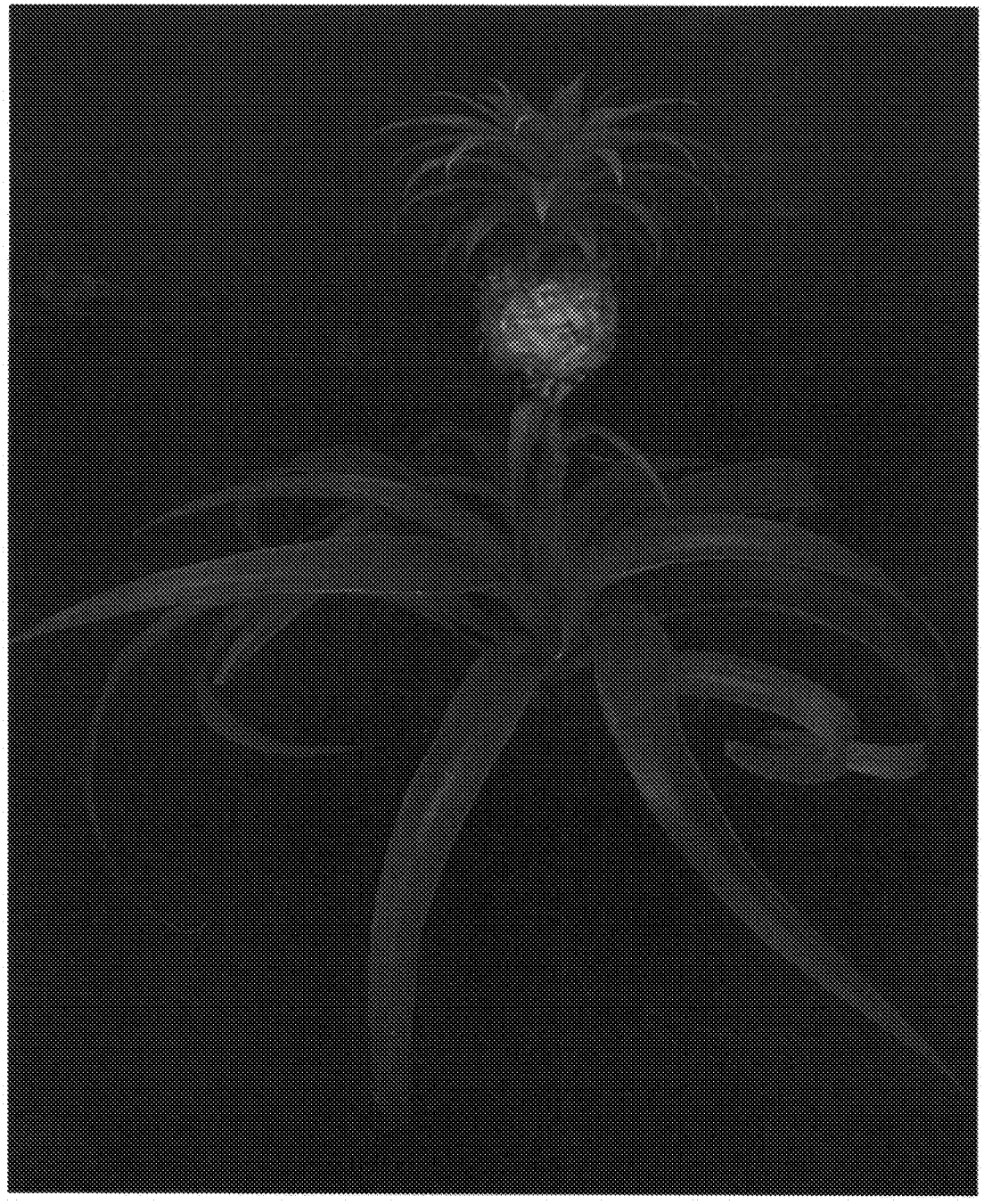

Latin name of the genus and species: *Ananas comosus.*
Variety denomination: 'Duranas'.

BACKGROUND OF THE INVENTION

The new cultivar is a product of a planned breeding program. The new variety originated from a cross pollination of an unnamed proprietary seedling of *Ananas comosus* with a different unnamed proprietary seedling of *Ananas comosus.* The new variety was discovered by the inventor, Chester Skotak Jr., a citizen of Costa Rica, in Ajauela, Costa Rica during June of 2005, in a group of seedlings resulting from the crossing.

Asexual reproduction of the new cultivar 'Duranas' was first performed in Costa Rica by vegetative cuttings, in January 2006. Propagation was subsequently performed by tissue culture in November 2006. 'Duranas' has since produced several generations by tissue culture and has shown that the unique features of this cultivar are stable and reproduced true to type.

SUMMARY OF THE INVENTION

The cultivar 'Duranas' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Duranas' These characteristics in combination distinguish 'Duranas' as a new and distinct *Ananas comosus* cultivar:

1. Compact, bushy plant shape.
2. Small fruit.
3. Suitability as an indoor pot plant.

Plants of the new cultivar 'Duranas' are similar to both parent varieties in some horticultural characteristics. However, 'Duranas' differs from both the seed and pollen parents in having a smaller fruit and shorter leaves.

COMMERCIAL COMPARISON

'Duranas' is best compared to the unpatented commercial variety *Ananas comosus* 'Champaca.' Plants of 'Champaca' are similar to plants of 'Duranas' in most horticultural characteristics, however, 'Duranas' has a more compact and bushy plant shape. 'Duranas' also has a lighter leaf color, shorter leaf and smaller fruit. Additionally the fruit of 'Duranas' is lighter in color than that of 'Champaca.'

BRIEF DESCRIPTION OF THE PHOTOGRAPH

The accompanying photograph in FIG. 1 illustrates in full color a typical plant of 'Duranas' grown in a greenhouse. This plant is approximately 9 months old, shown in an 12 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Duranas' plants grown in a climate controlled greenhouse in Alajuela, Costa Rica. Temperatures ranged from 20° C. to 24° C. night and day. No artificial light, photoperiodic treatments or chemical treatments were given to the plants. Measurements and numerical values represent averages of typical plant types.

Botanical classification: *Ananas comosus* 'Duranas.'

PROPAGATION

First propagation method: Cuttings
Type of propagation typically used: Tissue Culture Time to initiate roots: About 90 days at approximately 24° C.
Time to produce a rooted cutting/liner: About 90 days at approximately 24° C.

PLANT

Growth habit: Basal rosette with inflorescence growing from the centre
Height: Average: 27.3 cm
Plant spread: Average: 43.4 cm
Normal pot size: 12 cm
Growth rate: Low to moderate
Branching characteristics: Basal rosette
Quantity of leaves: Average 28 per rosette

FOLIAGE

Leaf:
*Arrangement.*—Placed in a basal rosette.
*Average length.*—Approximately 27.5 cm.
*Average width.*—Approximately 1.4 cm (measured at mid-section).
*Shape of blade.*—Linear.
*Aspect.*—Curved downward, slightly twisted.
*Apex.*—Long acuminate.
*Base.*—Sheath length: Average 2.1 cm. Sheath width: Average 2.4 cm. Sheath color: Near RHS Yellow-Green 150D, covered with a silvery-transparent layer, not measurable with R.H.S.-Colour Chart.
*Margin.*—Entire, sheath very finely and sharp serrate.
*Texture of top surface.*—Smooth, glossy.
*Texture of bottom surface.*—Smooth, dull.
*Color.*—Young foliage upper side: Near RHS Yellow-Green 143A, base lighter, both Yellow-Green 144B and 144C. Young foliage under side: Near RHS Green 137A, base lighter both Yellow-Green 144B and 144C. Under side covered with a waxy layer; near RHS Greyed-Green 192D and lighter. Mature foliage upper side: Near RHS Yellow-Green 144A. Mature foliage under side: Near RHS Yellow-Green 144D.
*Venation.*—Type: parallel. Venation coloration: Indistinguishable from leaf surface.
Petiole: No petioles present

INFLORESCENCE

General description:
*Inflorescence height, excluding scape.*—Approximately 12.5 cm.
*Inflorescence width.*—Approximately 14.4 cm.
Scape:
*Length.*—Approximately 14.9 cm.
*Width.*—Approximately 0.7 cm.
*Aspect.*—Approximately 90° angle to rosette (0°=horizontal).
*Strength.*—Very strong.
*Color.*—Near RHS Yellow-Green 144A, sparsely covered with a silvery-transparent layer not measurable with R.H.S. Colour Chart.
Bracts:
*Scape/lowermost bracts.*—Shape: linear. Length: Approximately 6.2 cm, excluding sheath. Width: Approximately 0.6 cm. Quantity: Average 5. Tip: narrow acuminate. Base: decurrent. Sheath length: Approximately 0.5 cm. Sheath width: Approximately 0.9 cm. Sheath color: Near RHS Yellow-Green 151A. Margin: Color Upperside: Near RHS Yellow-Green 144A, heavily tinged Greyed-Orange 174C and 174D near the base. Color Underside: Near RHS Yellow-Green 144B, tinged Greyed-Orange N170D near the base.
*Terminal bracts.*—Shape: linear-lanceolate. Length: Approximately 5.9 cm, excluding sheath. Width: Approximately 1.4 cm. Quantity: Average 75. Tip: acuminate. Base: decurrent. Sheath length: Approximately 1.1 cm. Sheath width: Approximately 2.2 cm. Sheath color: Near RHS Yellow-Green 145C and 145D, covered with a silvery-transparent layer not measurable with R.H.S. Colour Chart. Margin: Coloration Terminal Bracts: Upperside: Near RHS Green 137A sparsely covered with a silvery-transparent layer not measurable with R.H.S. Colour Chart. Underside: Near RHS Yellow-Green 144A, covered with a silvery-transparent layer not measurable with R.H.S. Colour Chart.

OTHER CHARACTERISTICS

Fruit/production: Typical *Ananas* fruits, relatively small, oblong and oblong in shape are produced. Average fruit length: about 4.6 cm, average fruit width: about 4.3 cm. Fruit color is a range between RHS Green 143A to the Yellow-Green 144B.
Disease resistance: Neither resistance nor susceptibility to diseases or pests has been observed in this variety.
Drought tolerance and cold tolerance: Observed to tolerate temperatures to 40° C. without any negative effects. Temperature tolerance above this range has not been observed. Tolerance of cold temperatures has not been observed.
Fruit/seed production:
*Fruitlets per fruit.*—Average: 31.
Fruit color (outside):
*Immature fruit color.*—Both RHS Green 143A and Yellow-Green 143A.
*Ripe fruit color.*—Background of both RHS Green 143A and Yellow-Green 143A tinged with Greyed-Orange 176A and 176B.
*Fruit flesh color.*—Near RHS Green-White 157C and Yellow-Green 150D near the center, changing to Yellow-Green 145C, 145B and 145A towards the outside.
*Flesh aroma.*—Non-aromatic.
*Fruit core average size and color.*—Average length of core: 3.5 cm, average diameter of core at the base: 5 mm, average diameter of core at the top: 1.1 cm, core colored near RHS Yellow-Green 144D.

What is claimed is:

1. A new and distinct cultivar of *Ananas comosus* plant named 'Duranas' as herein illustrated and described.

* * * * *